(12) United States Patent
Kyriakou (10) Patent No.: US 9,918,688 B2
(45) Date of Patent: Mar. 20, 2018

(54) DETERMINING A TISSUE PARAMETER (71) Applicant: Yiannis Kyriakou, Spardorf (DE)

(72) Inventor: Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 510 days.

(21) Appl. No.: 14/609,200

(22) Filed: Jan. 29, 2015

(65) Prior Publication Data
US 2015/0208996 A1    Jul. 30, 2015

(30) Foreign Application Priority Data

Jan. 29, 2014  (DE) .................. 10 2014 201 556

(51) Int. Cl.
*A61B 6/00* (2006.01)
*G06T 7/00* (2017.01)
*G06T 7/11* (2017.01)
*A61B 6/03* (2006.01)

(52) U.S. Cl.
CPC .............. *A61B 6/504* (2013.01); *A61B 6/481* (2013.01); *A61B 6/486* (2013.01); *G06T 7/0012* (2013.01); *G06T 7/0016* (2013.01); *G06T 7/11* (2017.01); *A61B 6/032* (2013.01); *A61B 6/4441* (2013.01); *A61B 6/5217* (2013.01); *G06T 2207/10016* (2013.01); *G06T 2207/10116* (2013.01); *G06T 2207/30104* (2013.01)

(58) Field of Classification Search
CPC combination set(s) only.
See application file for complete search history.

(56) References Cited

U.S. PATENT DOCUMENTS

| 7,974,679 | B2 * | 7/2011 | Zhou | ................ G01R 33/56518 324/307 |
| 8,045,780 | B2 * | 10/2011 | Boese | .................. G06T 11/008 382/131 |

(Continued)

OTHER PUBLICATIONS

German Office Action for German Application No. 10 2014 201 556.1, dated Aug. 22, 2014, with English Translation.

(Continued)

*Primary Examiner* — Anand Bhatnagar
(74) *Attorney, Agent, or Firm* — Lempia Summerfield Katz LLC (57) ABSTRACT

A method for determining a tissue parameter of tissue that may be determined from passage of a contrast agent through the tissue based on a series of temporally consecutive two-dimensional digital subtraction angiography x-ray images showing propagation of the contrast agent in the tissue over time and a vascular system present in a region of the tissue includes locating at least some of the vessels of the vascular system by segmentation in the x-ray images. The method also includes assigning pixels showing segmented vessels an interpolation intensity determined by interpolation from intensities of at least some of the pixels bordering the segmented vessel, so that x-ray images from which vessels have been eliminated result. The method includes determining tissue parameters for at least some of the pixels of the series of x-ray images from which the vessels have been eliminated.

21 Claims, 5 Drawing Sheets

(56) References Cited

U.S. PATENT DOCUMENTS

| | | | |
|---|---|---|---|
| 8,285,014 B2* | 10/2012 | Lauritsch | A61B 6/4441 378/4 |
| 2005/0113679 A1* | 5/2005 | Suryanarayanan | G06T 7/187 600/425 |
| 2005/0196028 A1* | 9/2005 | Kleen | A61B 8/483 382/128 |
| 2005/0249391 A1* | 11/2005 | Kimmel | G06T 7/143 382/128 |
| 2008/0107315 A1* | 5/2008 | Kimmel | G06T 7/143 382/128 |
| 2008/0137924 A1* | 6/2008 | Boese | G06T 11/008 382/128 |
| 2008/0247503 A1* | 10/2008 | Lauritsch | A61B 6/4441 378/4 |
| 2013/0131507 A1* | 5/2013 | Salazar-Ferrer | A61B 6/486 600/431 |
| 2015/0302584 A1* | 10/2015 | Brauner | A61B 6/508 382/128 |
| 2017/0027444 A1* | 2/2017 | Rege | A61B 3/0008 |

OTHER PUBLICATIONS

Siemens AG, Medical Solutions, Angiography, Fluoroscopic and Radiographic Systemssyngo iFlow / Dynamic Flow Evaluation / Answers for life.Order No. A91AX-20902-11C1-7600 | Printed in Germany | CC AX WS 12081.5 | 12.2008, Siemens AG; 2008.

\* cited by examiner

DETERMINING A TISSUE PARAMETER

This application claims the benefit of DE 10 2014 201 556.1, filed on Jan. 29, 2014, which is hereby incorporated by reference in its entirety.

BACKGROUND

The present embodiments relate to determining a tissue parameter.

In angiography, it is known to administer contrast agent that may be clearly identified in images (e.g., x-ray images) and therefore allows an assessment of the blood flow and the passage of blood through the vascular system of a patient and also through the tissue. One conventional method for tracking the propagation of the contrast agent is digital subtraction angiography. With this, a mask image is recorded without contrast agent. After this, raw images are recorded, frequently as a temporal series in a time range during which the contrast agent passes through the target region or vascular system of interest. The contrast agent may also be seen in these raw images. In order to remove the anatomy causing interference during the analysis, digital subtraction angiography x-ray images are produced by removing the mask image from the raw image so that image information that essentially only relates to the contrast agent remains. In order to achieve better orientation, two-dimensional digital subtraction angiography may be performed from a number of projection directions (e.g., using a biplane system). This may provide raw images and mask images of the target region from, for example, perpendicular projection directions, so that x-ray images are obtained for these perpendicular projection directions and may be viewed and analyzed for diagnosis purposes.

Two-dimensional subtraction angiography-x-ray images may be used to determine a plurality of time parameters, which show the behavior of the contrast agent or are derived therefrom, when the time-intensity curves TIC in the x-ray images are considered. In this process, the image data (e.g., intensity) of the x-ray image for all the time points of the series for which an x-ray image is available is plotted against recording times, at least for some image points/regions of interest, producing a time/intensity curve that may also be referred to as a contrast agent curve. This is accessible for conventional analysis methods. For example, the time up to the maximum contrast agent concentration at the image point may therefore be considered (e.g., the "time to peak" (TTP)). A further, frequently considered time parameter is the mean transit time MTT, which may be defined in different ways (e.g., relative to the maximum value of the time/intensity curve).

Contrast agent-assisted examinations are also particularly important with respect to the human brain (e.g., with regard to the passage of blood through the parenchyma). In order to examine this, regions of interest (ROI) may be defined in the subtraction angiography-x-ray images, which are as far as possible not overlaid by larger vessels. Integration over the time/intensity curve provides information relating to the quantity of contrast agent that has flowed through at an image point. When the time/intensity curve is considered for an entire region of interest, this applies to all the structures through which the x-rays pass there. This allows the cerebral blood volume (CBV) and the cerebral blood flow (CBF) to be derived (e.g., relative to a reference region). Specifically, the procedure may be described such that the area A below the time/intensity curve I(t) is first determined as $$A = \int_0^T I(t)dt.$$

The contrast agent concentration C is now proportional to A. The cerebral blood volume CBV is defined as proportional to $$CBV \propto \frac{C_{ROI}}{Cy_{Artery}}.$$

If a reference region (reference ROI) is now added, the resulting relative blood volume rCBV is $$rCBV \propto \frac{A_{ROI}}{A_{ref}}.$$

The reference ROI here does not have to originate from the x-ray image itself, with "left/right" comparisons also frequently being performed, but may also originate from an angiography data record and the like recorded before an intervention. The corresponding rCBF may also be determined using a suitable conversion.

In the prior art, tools were already known to help a user with the analysis of two-dimensional subtraction angiography-x-ray images (e.g., for images recorded using a biplane x-ray facility).

SUMMARY AND DESCRIPTION

The scope of the present invention is defined solely by the appended claims and is not affected to any degree by the statements within this summary.

Time parameters are determined in each instance for the individual x-ray images from the time/intensity curves and are color-coded, for example, or displayed by way of a gray value scale (e.g., color-coding systems, in which a red color is assigned to early TTPs, a yellow to green color is assigned to middle TTPs, and a blue color is assigned to high TTPs). Such display options also exist for tissue parameters, as it may be relevant for certain medical questions only to look at the perfusion or passage of blood through the parenchyma (e.g., through the brain parenchyma). Examples of these are examinations after a stroke or in the event of a vasospasm. However, the options known in the prior art do not allow tissue parameters to be displayed reliably or for the entire x-ray image, as the large vessels of the vessel tree overlay the parenchyma, and high contrast agent concentrations occur there. Other options for arriving at such tissue parameters are three-dimensional perfusion recordings, which, however, are not always desirable due to the expenditure incurred.

The present embodiments may obviate one or more of the drawbacks or limitations in the related art. For example, an option for the improved determination of tissue parameters from two-dimensional DSA x-ray images is provided.

A method for at least some of the vessels of the vascular system to be located by segmentation in the x-ray images is provided. Pixels showing segmented vessels are assigned an interpolation intensity determined by interpolation from the intensities of at least some of the pixels bordering the segmented vessel, so that x-ray images from which vessels have been eliminated result. The tissue parameters are determined for at least some of the pixels of the series of x-ray images from which vessels have been eliminated.

The tissue parameters, which are then available as a map, may be shown, for example, as a color-coded representation. For example, relative color-coded blood volume maps and relative color-coded blood flow maps may therefore be provided. A relative blood volume and/or a relative blood throughflow may therefore be determined as a tissue parameter. The determination of such parameters is based on an image series from which components of vessels have at least largely been eliminated, and therefore, a time/intensity curve.

The interfering components of large vessels are minimized, so that the tissue parameters may be determined more reliably over all the x-ray images of the series. This reduces the influence of the large vessels and gives more weight to the parenchyma components. In principle a similar procedure to the one for metal artifact correction is provided, in that the vessels are segmented, and interpolation is then performed for the corresponding pixels. However, in one or more of the present embodiments, the temporal component is a difference. Vessels may only be identified clearly (and therefore only interfere) in some x-ray images due to the contrast agent, which is also taken into account in the context of one or more of the present embodiments by temporal segmentation. Whether there is a vessel present at a certain point may be less important than whether the vessel is filled with contrast agent and therefore interferes with the determination of the tissue parameter. Contrast agent-filled vessels of the vascular system are segmented. Depending on the segmentation, not only does a 2D interpolation result but also a (2D+t) interpolation. There is therefore a reduction in the influence of the vessel filling on the measured blood volume, which is used to determine maps of the tissue parameter with the smallest possible degree of overlaying.

The method of one or more of the present embodiments may advantageously be performed totally automatically and may be applied to any DSA 2D series. A representation of vessel parameters correlating with three-dimensional perfusion recordings results.

When tissue parameters referenced to a region in the x-ray images of the series are determined, the region used as the reference region for the determination of the relative tissue parameters may be a region containing no segmented vessels or a minimized number of segmented vessels. The reference region is then affected as little as possible by the interpolation and, for example, supplies extremely reliable values.

During segmentation of the vessels, at least one intensity threshold value may be used to differentiate tissue intensities and vessel intensities. This provides that intensity threshold values are determined, by way of which the vessel filling may be differentiated from the tissue filling. In one embodiment, the intensity threshold value may be determined at least partially (e.g., completely automatically and/or relative to a maximum intensity in a supplying artery). A supplying artery (e.g., in the case of recordings of the human brain, the carotid artery) may easily be located automatically and has the highest contrast agent concentration that will occur. The intensity threshold value may therefore be determined particularly easily relative to the filling in the largest artery. The intensities occurring over time and the propagation of the contrast agent may be analyzed for the automatic determination of the intensity threshold value. It is known, for example, that very high intensities occur initially in the arteries due to the contrast agent, while the intensities in the veins are lower during discharge, so a lower threshold value results. Intensity regions that may be used for assignment to the parenchyma or to a filled vessel may thus be defined. In one embodiment, the intensity threshold value is determined automatically from a consideration of the intensities occurring over time (e.g., based on an identification of an arterial phase and a venous phase).

In one embodiment, a time-dependent intensity threshold value is defined (e.g., different intensity threshold values are determined for an arterial phase, a venous phase and a tissue phase). The greatest contrast agent concentration occurs at the time point at which the contrast agent bolus passes through the supplying artery into the recorded target region, after which the contrast agent is distributed to the increasingly small arteries, flows through the tissue and is transported away again through the veins with a much lower intensity. This provides, however, that intensity threshold values that differ over time may be provided in order to be able to differentiate the tissue from the vessels that are filled with contrast agent. For example, a temporal division into three categories may be provided (e.g., an arterial phase, a tissue phase and a venous phase). However, more specific divisions may also be provided (e.g., the determination of an intensity threshold value for each time point for which an x-ray image is available in the series).

The segmentation and interpolation may take place such that a maximum time point of maximum intensity is defined for each pixel or, if a different x-ray image division is selected, each image segment (e.g., if the maximum intensity present exceeds the intensity threshold value, when a time-dependent intensity threshold value is used, the intensity threshold value assigned to the maximum time point, for every time point for which an x-ray image is available, within a time interval extending around the maximum time point, at least two adjacent pixels or adjacent image segments as closely adjacent as possible to the pixel or image segment in question being located, the image data of which is below the intensity threshold value; when a time-dependent intensity threshold value is used, the intensity threshold value assigned to the time point, and an intensity interpolated from the adjacent pixels or adjacent segments being assigned to the pixel or image segment in question). Therefore, if larger image segments that contain a number of pixels are to be considered, for each pixel or each image segment, the maximum time point is located. At the maximum time point, the greatest intensity is present in the pixel or image segment over the entire series of x-ray images. This pixel or image segment is then the vessel pixel or vessel image segment, when the maximum intensity exceeds the intensity threshold value, where applicable at the maximum time point. If this is the case, a segmentation of the local vicinity is performed for this pixel or image segment (e.g., according to the "region growing" method), with the intensity threshold value assigned where applicable to the maximum time point again being taken into account. Once at least two pixels or image segments that are no longer to be assigned to a vessel filled with contrast agent but to the tissue have been located, the values of these adjacent pixels or adjacent image segments may be used to perform a 2D interpolation and to replace the value for the pixel or image segment in question. As at adjacent time points the intensity threshold value corresponding where applicable to the adjacent time point may also still be exceeded, the procedure is also extended temporally to a time interval around the maximum time point in order to allow the replacement in a correct manner there. This produces a 2D+t interpolation.

In one variant, the interpolation is also performed for vessel pixels or vessel image segments located between the pixel or image segment in question and the adjacent pixels or adjacent image segments. The interpolated values are used for the analysis of the next pixel or image segment to be considered. This provides that an interpolation always takes place at least in the local vicinity of a located vessel point, which avoids individual consideration of the other pixels later. These have already been processed together with a previously considered pixel or image segment and should now no longer exceed the intensity threshold value. A region growing segmentation, as discussed above, proves extremely useful here for locating pixels or image segments for which an interpolation is to be performed. Which pixels or image segments were detected as being associated with vessels (e.g., contrast agent-filled) may be recorded in the protocol during the course of segmentation and interpolation.

The time interval is selected, if the time interval is defined as a transit time of the contrast agent determined from the time/intensity curve of the pixel or image segment in question or as all the time points at which the intensity of the pixel or image segment in question exceeds the intensity threshold value, when a time-dependent intensity threshold value is used the intensity threshold value assigned to the time point. This captures all the time points at which the pixel or image segment may be identified as showing a vessel filled with contrast agent. The segmentation is thus extended in the time dimension, which then also applies to the interpolation.

A segmentation according to the TTP (which corresponds to the maximum time point) may also be provided. There are, however, overlap regions in which the arteries have already supplied some of the contrast agent to the tissue, but more remote arteries do not yet contain contrast agent themselves.

Other segmentation methods (e.g., vessel tree-based segmentation methods, segmentation methods taking into account a three-dimensional image data record registered with the x-ray images, at least partially manual segmentation methods and the like) for locating vessel pixels or vessel image segments and after which the interpolation may then take place may be provided.

The interpolation may take place in a linear manner or using a spline function (e.g., a thin plate spline function). However, other types of interpolation that may attempt at least some degree to supplement more complex relationships and structures as correctly as possible may also be provided.

In one embodiment, a vessel model is created from pixels segmented as showing a vessel. The vessel model is shown for orientation together with these, for example, when showing the tissue parameters. This provides for the identification of vessel pixels (or vessel image segments) being used not only for interpolation and therefore "vessel elimination", but because vessels are definitely identified, also for creating a vessel model. During the interpolation process, all the pixels or image segments, which were identified as being associated with a vessel at one time point at least, may also be recorded in the protocol and form the vessel model. In a further processing act, boundaries of vessels and/or corresponding center lines may, for example, be defined in order to allow a representation of the vessel model. Because of the temporal segmentation, different vessels in the vessel model may be differentiated between in that, for example, the TTP is examined for jumps in a local vicinity and so on.

The x-ray images from which vessels have been eliminated may be divided into image segments, for which the tissue parameter is determined, using a grid in order to determine the tissue parameters. In order to average out local noise fluctuations and/or to eliminate other measurement errors for individual points from the analysis where possible, it is known in the prior art to determine tissue parameters for larger regions (ROIs). For example procedures are known in the prior art in which there is manual selection of ROIs that, in the user's opinion, have the smallest possible influence due to overlaid blood vessels. As the method allows a clear reduction in the influence of the blood vessels over the entire image, the division into regions may be defined based on a grid to be laid over the x-ray images from which vessels have been eliminated as image segments (e.g., square and contain a certain number of pixels). Image segments that may also be defined by way of such a grid (e.g., if necessary the same grid) may be used for the interpolation, as indicated.

An embodiment results if the determination of tissue parameters takes place for different positions of the grid, with the final tissue parameter assigned to a pixel being determined by combination (e.g., by forming a mean value, from the tissue parameters determined in different grid positions). In one embodiment, different grid positions and, therefore, differently defined image segments that accordingly overlap at least partially may be determined. If mean values of the contributing image segments are now used in the overlap regions, a smoothed end result, which is less influenced by statistical fluctuations, results for the tissue parameters. The grid movement between different grid positions may take place in a certain direction, but different movement directions with respective grid positions may also be provided. In this embodiment, each image segment forms a sort of sliding window so that generally reference may be made to a method that uses a sliding grid.

In addition to the method, one or more of the present embodiments relate to an x-ray facility (e.g., an x-ray device) including a control facility (e.g., a controller or a processor) configured to perform the method. All the embodiments relating to the method may be applied in a similar manner to the x-ray facility. The x-ray facility may be an angiography x-ray facility (e.g., an x-ray facility with a C-arm) that may be moved to a certain angulation in relation to the patient in order to record the mask images and raw images used for the digital subtraction angiography x-ray images. In one embodiment, biplane x-ray facilities, with which two recording arrangements are provided, may be used. Each of the two recording arrangements includes an x-ray detector and an x-ray emitter that may be arranged at different angulations (e.g., each being assigned to its own C-arm). X-ray images may thus be produced from different projection directions. Both series of x-ray images resulting in this manner may be analyzed using the method.

In one embodiment, the control facility may therefore include a segmentation unit for segmenting vessels of the vascular system in the x-ray images, an interpolation unit for interpolating with vessel pixels or vessel segments, and a tissue parameter determination unit for determining the tissue parameters. Further function units, which may be provided, are recording units for the specific recording of the x-ray images and a display unit that may display a representation of the tissue parameters (e.g., overlaid with a vessel model).

One or more of the present embodiments relate to a computer program that performs the acts of the method when the computer program is executed on a computation facility (e.g., a computer). The computation facility may be, for example, the control facility of an x-ray facility. All the embodiments relating to the method may also be applied in a similar manner to the computer program. The computer program may be stored on a non-transient computer-readable data medium (e.g., a CD ROM).

DETAILED DESCRIPTION

Exemplary embodiments of the method to be discussed in the following are for the determination of tissue parameters in the human brain (e.g., a relative cerebral blood volume and a relative cerebral blood flow (rCBV and rCVF)). An examination of the head of a patient is therefore considered here. The object of the examination is the parenchyma. As a basis, the method uses a series of digital subtraction angiography x-ray images, with a mask image first being recorded for each considered projection direction (e.g., two projection directions in the case of biplane examinations), for example, before the administration of the contrast agent after the patient has been positioned. After the administration of the contrast agent, a time series of raw images is recorded, showing the propagation of the contrast agent in the vascular system (e.g., the vascular system of the brain) and in the tissue. In digital subtraction angiography, to determine the x-ray images, the mask image recorded in the same projection direction is subtracted from each raw image in the time series so that the anatomy component is at least largely eliminated, and only the components originating from the contrast agent remain. The contrast agent-filled vessels or the contrast agent-filled tissue may thus be clearly identified.

Figure 1:
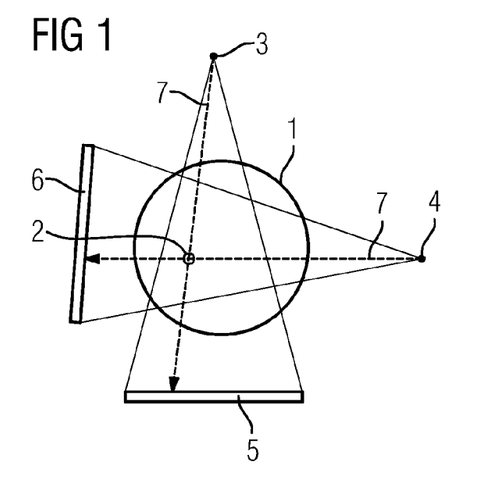
FIG. 1 shows a biplane recording.

One possible geometry for recording such x-ray images is shown in FIG. 1. An object 1 is to be recorded there (e.g., a target region in the form of the vascular system of interest and tissue), with a contrast agent-filled vessel 2 shown prominently by way of example. The biplane x-ray facility used, for example, includes two recording arrangements, each having an x-ray emitter 3, 4 and an x-ray detector 5, 6. The projection directions of the x-ray detector 5, 6 are perpendicular to one another for the purpose illustrated here. As shown by the arrows 7, the vessel 2 is projected onto different points of the respective x-ray detector 5, 6, where the vessel 2 therefore also shows in the x-ray image.

Figure 2:
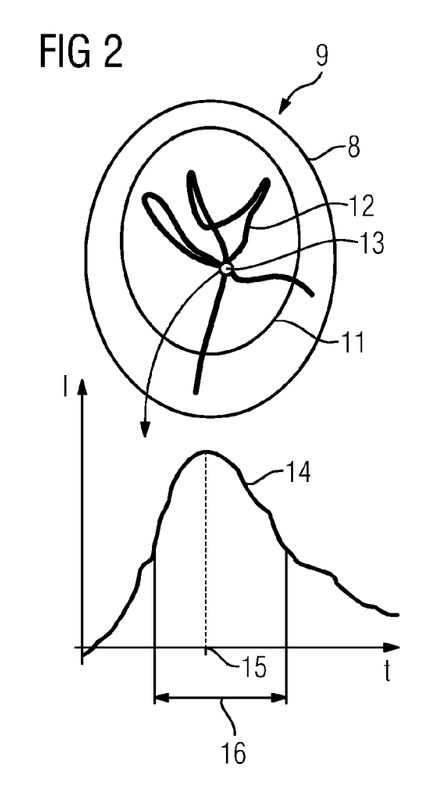
FIG. 2 shows an exemplary x-ray image with an assigned time/intensity curve in one projection direction.

FIG. 2 shows a rough basic outline of the fundamental structure of one embodiment of an x-ray image 9, with the possible outer edge 8 of the skull of a patient only being shown for orientation, as the corresponding signal is no longer contained in the x-ray image 9 after digital subtraction angiography has been performed. The x-ray image 9 shows both the parenchyma 11, in which the contrast agent is distributed, therefore present with a lower concentration, and the vascular system shown as 12. Looking at a certain point or pixel 13 or the intensity measured there over the time series produces a time/intensity curve 14. The time/intensity curve 14 may be analyzed for time parameters but may also form the basis for the determination of tissue parameters. Examples of time parameters are the time 15 until the greatest contrast agent concentration (TTP) and the mean transit time 16, which may be defined in different ways (e.g., over half the intensity at the TTP 15, which is also referred to below as the maximum time point for a pixel 13). The methods for determining tissue parameters such as relative cerebral blood volume and relative cerebral blood flow for regions in the parenchyma have already been set out in the introduction.

Figure 3:
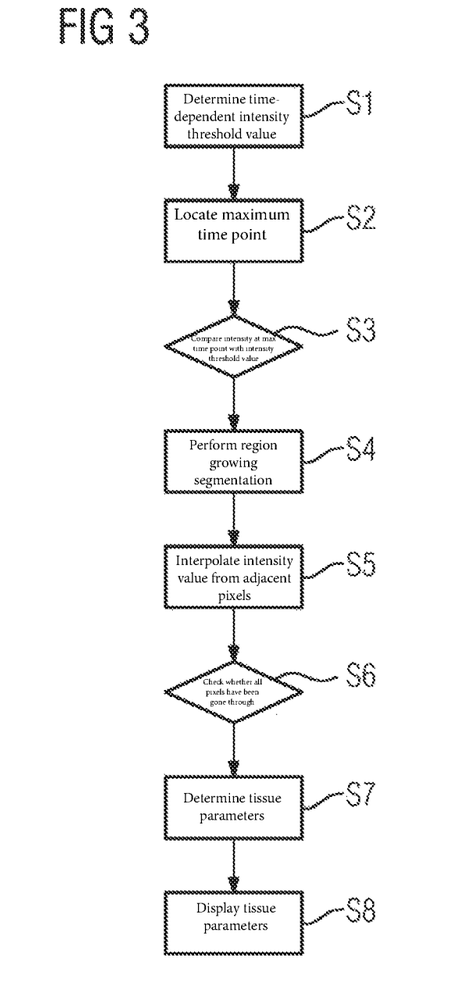
FIG. 3 shows a sequence of one embodiment of a method.

The method of one or more of the present embodiments, described in more detail in the following with reference to FIG. 3, specifies an option for determining the tissue parameters where possible over all the x-ray images and thereby reducing/minimizing the influences of contrast agent-filled vessels, which overlay the tissue.

In act S1, a time-dependent intensity threshold value is first determined for the time series of x-ray images. The intensity threshold value should allow differentiation between intensities as are present in vessels and intensities as are present in the tissue at the time points for which x-ray images are available. Such an intensity threshold value may be determined for any time point for which x-ray images are available or for certain time regions (e.g., for an arterial phase, a venous phase and a tissue phase). The greatest contrast agent concentration occurs at the time point at which the contrast agent bolus passes through the supplying artery into the recorded target region. The contrast agent is then distributed into the increasingly small arteries, flows through the tissue and is transported away again through the veins with a lower intensity. This progression of the propagation of the contrast agent may be analyzed automatically, starting from the arrival of the contrast agent bolus in the supplying artery (e.g., the carotid artery). This produces intensity threshold values that differ over time, which make it possible to differentiate the tissue from the vessels that are filled with contrast agent.

In act S2, a first pixel (or optionally also image segment including a number of pixels, if such a division is selected) of the x-ray images of the series is selected, and the corresponding time/intensity curve 14 is considered, to locate the maximum time point (e.g., the time point 15 of the maximum contrast agent concentration). In act S3, the intensity at the maximum time point is compared with the intensity threshold value assigned to the maximum time point, as determined in act 51. If it is ascertained in this comparison that it may be a tissue pixel, the method continues with the next pixel in act S2. However, if a vessel pixel is identified, the method continues in act S4.

The acts S4 and S5 that now follow are performed for each x-ray image in a time interval around the maximum time point. The time interval is defined as including all the time points at which the intensity of the pixel in question exceeds the intensity threshold value assigned to the time point. The time interval therefore relates to all the time points at which the pixel would be classified as a vessel pixel.

In act S4, a region growing segmentation is performed starting from the pixel in question identified as a vessel pixel, until at least two adjacent pixels assigned to the tissue and located as closely as possible to the pixel in question are located therefore do not exceed the intensity threshold value assigned to the time point. This is explained in more detail in relation to FIG. 4, which shows a section 17 of an x-ray image 9 at a considered time point. The currently considered pixel 18 is marked with an "X" and lies within the path of a vessel shown with a broken line 19. Starting from the pixel 18 in question, further vessel pixels in the vicinity are now located in the region growing algorithm. The further vessel pixels also exceed the corresponding intensity threshold value and are shown shaded in FIG. 4. Pixels not shown shaded are tissue pixels that may be considered as adjacent pixels, in which the intensity value is therefore below the intensity threshold value for the time point of the section 17.

Figure 4:
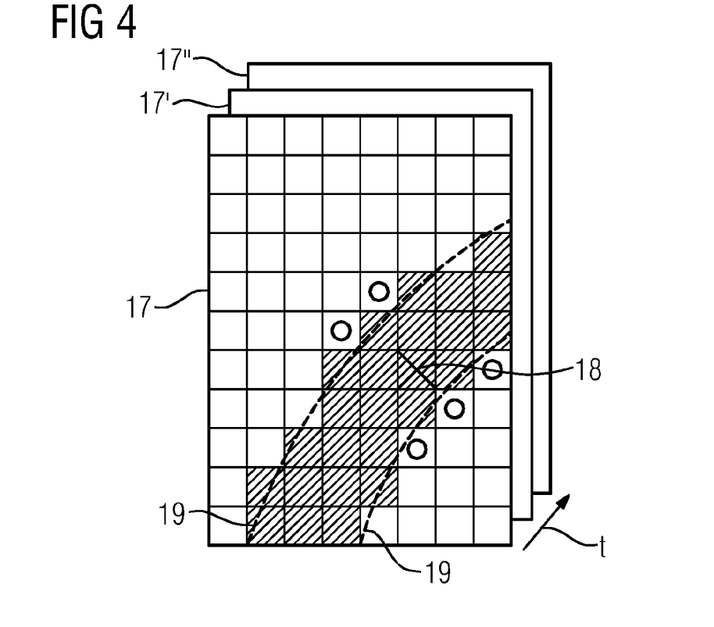
FIG. 4 shows a basic outline for an exemplary segmentation of vessel pixels.

For example the pixels marked with a circle in FIG. 4 may be used as adjacent pixels for the interpolation following in act S5 at the pixel 18 in question. The intensity value of the pixel 18 in question is then interpolated from the intensity values of the adjacent pixels (e.g., by an interpolation by way of thin plate splines). Other types of interpolation may also be provided.

In one embodiment, the interpolation may also be performed now for the other vessel pixels (shaded in FIG. 4) located in act S4 to achieve a more effective procedure, in which other adjacent pixels may also be used. Each pixel, which has been identified at any time point as a vessel pixel, is also marked and included in a vessel model that describes the path of the vessels.

To show that the segmentation and interpolation also take place in a temporal direction, temporally adjacent image sections 17' and 17" are also shown in FIG. 4.

Figure 5:
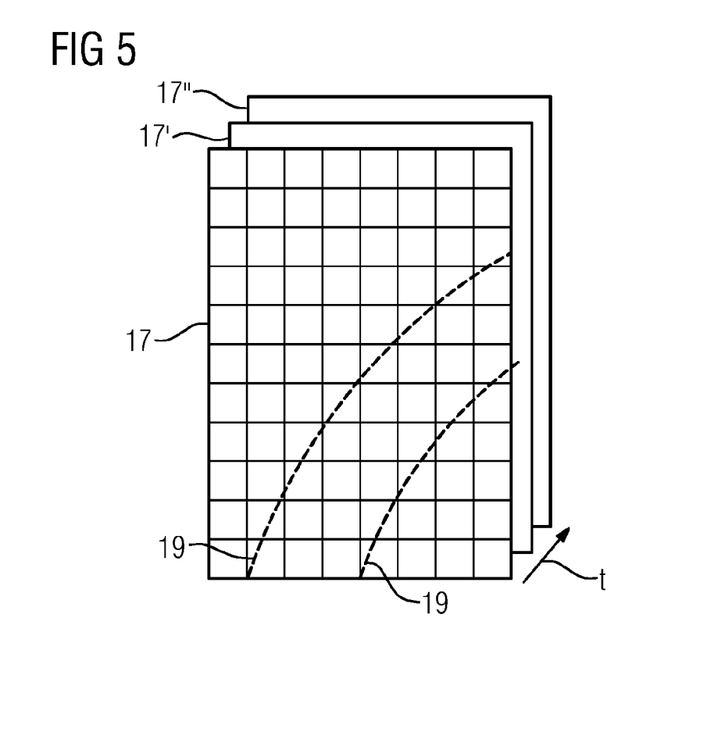
FIG. 5 shows an outline for an exemplary interpolation.

FIG. 5 shows a further basic outline of an exemplary result of the interpolation in act S5, from which it is shown that none of the pixels are now shaded. All the values are thus below the intensity threshold value, and overlaying by the vessel has been largely eliminated.

As this interpolation was performed for all the x-ray images in the time interval, in act S6, it is checked whether all the pixels in the x-ray image have already been gone through. If not, the method continues in act S3 for the next pixel.

Since all the vessel pixels have been located and an interpolation has been performed in this manner, the tissue parameters are determined in act S7. In principle, this does not take place pixel by pixel, but the determination takes place at least as an intermediate step over larger image segments (e.g., sectors). A division into image segments takes place, in that a grid 20, as shown in FIG. 5, is laid over the x-ray image 9, which is again only shown roughly. The grid defines image segments 21 that contain a certain number of pixels. One of the image segments 21 (e.g., the image segment 21a) is used as a reference image segment for determining the tissue parameters (e.g., the rCBV and rCBF). The image segment 21a is selected such that the image segment 21a contains no vessels if possible, so is influenced as little as possible by the interpolation.

Figure 6:
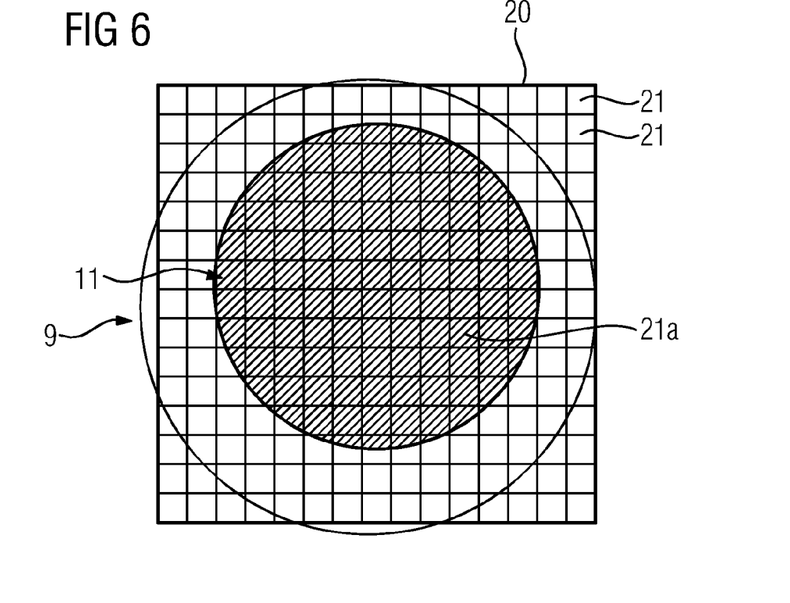
FIG. 6 shows an exemplary division of an x-ray image in a grid.

FIG. 6 shows an exemplary x-ray image 9 from which vessels have been eliminated (e.g., only the parenchyma 11 (the tissue of interest) may be identified as filled with contrast agent.

As known in the prior art, the rCBV and rCBF may now be determined for each image segment 21 by way of the area below the time/intensity curve 14 for the image segment in question and the reference image segment 21a.

Figure 7:
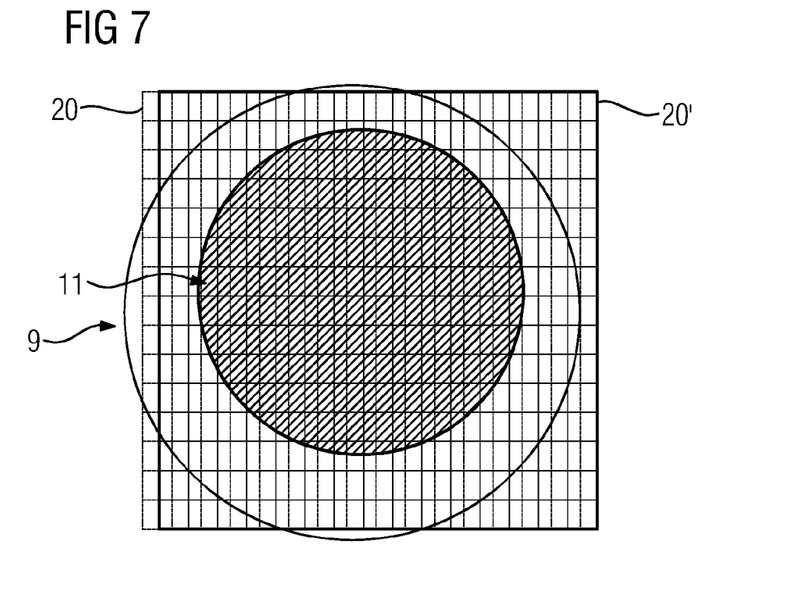
FIG. 7 shows an outline representing different exemplary grid positions.

In act S7, however, a spatially more precisely resolved determination of the tissue parameters is performed, in that a sliding grid 20 is used, as shown in FIG. 7, that in addition to the grid 20 in the position already shown in FIG. 6 (shown with a broken line), also shows the grid 20' in a relatively displaced position. This shows image segments overlapping with a number of image segments 21. This may be performed for a plurality of possible positions and therefore a plurality of possible image segments that overlap in different ways. An improved value may thus be determined for the tissue parameter for each pixel, for example, by forming the mean value of the image segments of the different grid positions containing said pixel.

Figure 8:
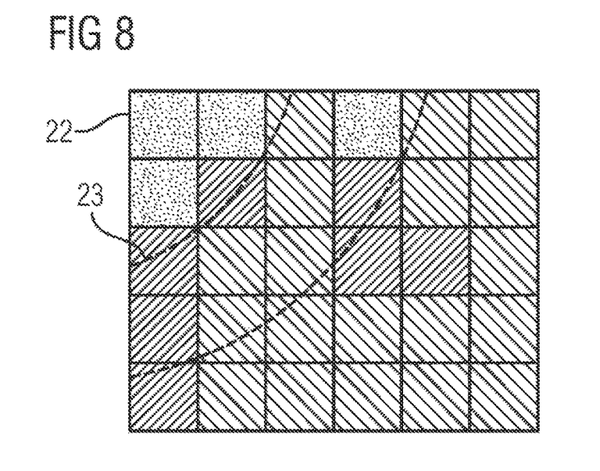
FIG. 8 shows a possible representation of the tissue parameters.

In act S8, the tissue parameter may be displayed as a two-dimensional representation (e.g., color-coded). A section 22 from such a representation is shown in FIG. 8. Pixels of different tissue parameters are shown in FIG. 8 in different colors, as shown by the different shading. For the purpose of orientation in the manner of a map, the representation also includes boundaries 23 of the segmented vessels, which were stored as the vessel model in act S4. As temporal information is also available, connected vessels may also be identified, and corresponding boundaries and/or center lines may therefore also be determined. This allows the representation of the tissue parameter to be extended.

Figure 9:
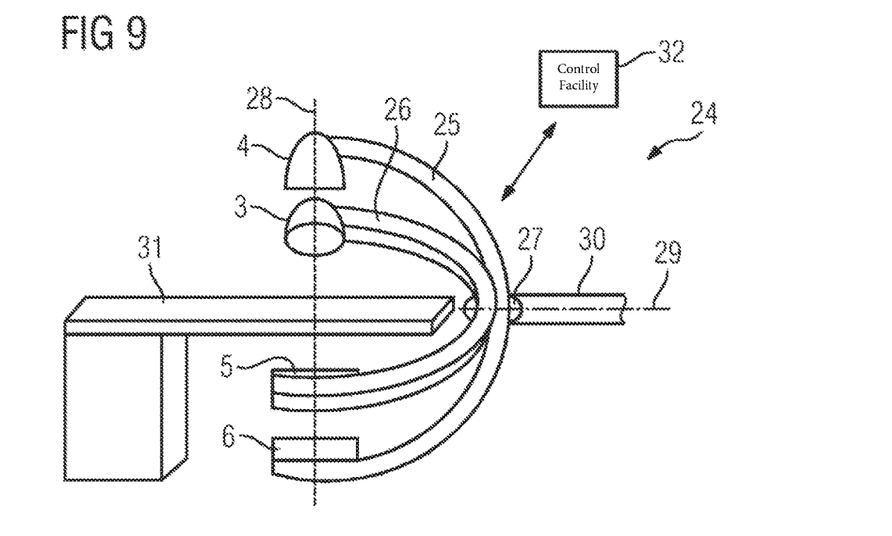
FIG. 9 shows one embodiment of an x-ray facility.

FIG. 9 shows one embodiment of an x-ray facility 24. This is a biplane x-ray facility that has two C-arms 25, 26. On each of the two C-arms 25, 26, an x-ray emitter 3, 4 and an x-ray detector 5, 6 are arranged opposite one another, as described. The C-arms 25, 26 may be rotated in a plane 28 about the rotation axis 29 by way of a pivot bearing 27. The C-arms 25, 26 are held by a support 30 that is merely indicated in FIG. 9. A patient couch 31 is provided to support a patient.

Operation of the x-ray facility 24 is controlled by a control facility 32 that is configured to perform the method and on which therefore a computer program, for example, is available.

Although the invention has been illustrated and described in detail using the exemplary embodiments, the invention is not limited by the disclosed examples, and other variations may be derived therefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a tissue parameter of tissue that is determinable from passage of a contrast agent through the tissue based on a series of temporally consecutive two-dimensional digital subtraction angiography x-ray images showing propagation of the contrast agent in the tissue over time and a vascular system present in a region of the tissue, the method comprising:

locating at least some vessels of the vascular system, the locating comprising segmenting in the x-ray images, wherein the segmenting in the x-ray images comprises:

determining, for a pixel, a maximum intensity over a time interval;

comparing the respective maximum intensity with at least one intensity threshold value; and identifying a type of intensity for the respective maximum intensity based on the comparison;

assigning pixels showing segmented vessels an interpolation intensity determined by interpolation from intensities of at least some pixels bordering the segmented vessel, so that x-ray images from which vessels have been eliminated result; and determining tissue parameters for at least some of the pixels of the series of x-ray images from which the vessels have been eliminated.

2. The method of claim 1, further comprising determining a relative blood volume, a relative blood throughflow, or the relative blood volume and the relative blood throughflow as the tissue parameters.

3. The method of claim 2, wherein a region containing no segmented vessels or a minimized number of segmented vessels is used as a reference region for the determination of the relative tissue parameters.

4. The method of claim 1, wherein during segmentation of the vessels, the at least one intensity threshold value is used to differentiate tissue intensities and vessel intensities.

5. The method of claim 4, wherein the at least one intensity threshold value is determined at least partially in a supplying artery.

6. The method of claim 5, wherein the at least one intensity threshold value is determined completely automatically, relative to a maximum intensity, or completely automatically and relative to the maximum intensity.

7. The method of claim 5, wherein the at least one intensity threshold value is determined automatically from a consideration of the intensities occurring over time.

8. The method of claim 7, wherein the at least one intensity threshold value is determined automatically from the consideration of the intensities occurring over time based on an identification of an arterial phase and a venous phase.

9. The method of claim 4, wherein a time-dependent intensity threshold value is defined for an arterial phase, a venous phase, and a tissue phase.

10. The method of claim 9, wherein different intensity threshold values are determined for an arterial phase, a venous phase, and a tissue phase.

11. The method of claim 4, wherein a maximum time point of maximum intensity present is defined for each pixel or, when a different x-ray image division is selected, each image segment, wherein when a maximum intensity present exceeds the intensity threshold value, when a time-dependent intensity threshold value is used, the intensity threshold value assigned to the maximum time point, for every time point for which an x-ray image is available, within a time interval extending around the maximum time point, at least two adjacent pixels or adjacent image segments as closely adjacent as possible to the pixel or image segment in question being located, the image data of which is below the intensity threshold value, and wherein when a time-dependent intensity threshold value is used, the intensity threshold value assigned to the time point, and an intensity interpolated from the adjacent pixels or adjacent segments being assigned to the pixel or image segment in question.

12. The method of claim 11, wherein the interpolation is also performed for vessel pixels or vessel image segments located between the pixel or image segment in question and the adjacent pixels or adjacent image segments, with the interpolated values being used for the analysis of the next pixel or image segment to be considered.

13. The method of claim 11, wherein the time interval is defined as a transit time of the contrast agent determined from a time/intensity curve of the pixel or image segment in question or as all time points at which the intensity of the pixel or image segment in question exceeds the intensity threshold value, or when a time-dependent intensity threshold value is used, the intensity threshold value assigned to the time point.

14. The method of claim 1, wherein the interpolation takes place in a linear manner or using a spline function.

15. The method of claim 14, wherein the interpolation takes place using a thin plate spline function.

16. The method of claim 1, further comprising creating a vessel model from pixels segmented as showing a vessel, the vessel model being shown for orientation together with the pixels segmented as showing the vessel when showing the tissue parameters.

17. The method of claim 1, further comprising dividing the x-ray images from which vessels have been eliminated into image segments, for which the tissue parameter is determined, using a grid to determine the tissue parameters.

18. The method of claim 17, wherein the determination of the tissue parameters takes place for different positions of the grid, with the final tissue parameter assigned to a pixel being determined by forming a mean value from the tissue parameters determined in different grid positions.

19. The method of claim 1, wherein the type of intensity for the respective maximum intensity comprises a tissue intensity or a vessel intensity.

20. An x-ray device comprising:

a controller for determining a tissue parameter of tissue that is determinable from passage of a contrast agent through the tissue based on a series of temporally consecutive two-dimensional digital subtraction angiography x-ray images showing propagation of the contrast agent in the tissue over time and a vascular system present in a region of the tissue, the controller being configured to:

locate at least some vessels of the vascular system, the locating comprising segmentation in the x-ray images, wherein the segmentation in the x-ray images comprises:

determination, for a pixel, of a maximum intensity over a time interval:

comparison of the respective maximum intensity with at least one intensity threshold value; and identification of a type of intensity for the respective maximum intensity based on the comparison;

assign pixels showing segmented vessels an interpolation intensity determined by interpolation from intensities of at least some pixels bordering the segmented vessel, so that x-ray images from which vessels have been eliminated result; and determine tissue parameters for at least some of the pixels of the series of x-ray images from which the vessels have been eliminated.

21. In a non-transitory computer-readable storage medium storing instructions executable by a computer to determine a tissue parameter of tissue that is determinable from passage of a contrast agent through the tissue based on a series of temporally consecutive two-dimensional digital subtraction angiography x-ray images showing propagation of the contrast agent in the tissue over time and a vascular system present in a region of the tissue, the instructions comprising:
  locating at least some vessels of the vascular system, the locating comprising segmenting in the x-ray images, wherein the segmenting in the x-ray images comprises:
    determining, for a pixel, a maximum intensity over a time interval;
    comparing the respective maximum intensity with at least one intensity threshold value; and
    identifying a type of intensity for the respective maximum intensity based on the comparison;
  assigning pixels showing segmented vessels an interpolation intensity determined by interpolation from intensities of at least some pixels bordering the segmented vessel, so that x-ray images from which vessels have been eliminated result; and
  determining tissue parameters for at least some of the pixels of the series of x-ray images from which the vessels have been eliminated.

* * * * *